(12) United States Patent
Pescher et al.

(10) Patent No.: US 7,638,055 B2
(45) Date of Patent: *Dec. 29, 2009

(54) SLUDGE QUALITY

(75) Inventors: Yvette Pescher, Paris (FR); Robert Talbot, Cannock (GB); Luc Louvel, Lyons (FR); Agnes Pilas-Begue, Saint-Romain (FR)

(73) Assignee: Rhodia Operations, Aubervilliers (FR)

( * ) Notice: Subject to any disclaimer, the term of this patent is extended or adjusted under 35 U.S.C. 154(b) by 8 days.

This patent is subject to a terminal disclaimer.

(21) Appl. No.: 11/630,604

(22) PCT Filed: Jun. 21, 2005

(86) PCT No.: PCT/GB2005/002439

§ 371 (c)(1),
(2), (4) Date: Nov. 2, 2007

(87) PCT Pub. No.: WO2005/123607

PCT Pub. Date: Dec. 29, 2005

(65) Prior Publication Data

US 2008/0135476 A1  Jun. 12, 2008

(30) Foreign Application Priority Data

Jun. 21, 2004 (WO) ............... PCT/GB2004/002656
Dec. 17, 2004 (GB) ................. 0427692.9

(51) Int. Cl.
*C02F 3/02* (2006.01)
*C02F 11/16* (2006.01)

(52) U.S. Cl. ................. 210/620; 210/631; 210/764; 422/28

(58) Field of Classification Search .................. 210/764
See application file for complete search history.

(56) References Cited

U.S. PATENT DOCUMENTS

| 4,673,509 | A | * | 6/1987 | Davis et al. ................. 210/699 |
| 4,966,716 | A | * | 10/1990 | Favstritsky et al. .......... 210/755 |
| 5,352,444 | A | | 10/1994 | Cox et al. |
| 5,385,896 | A | * | 1/1995 | Bryan et al. ................. 514/129 |
| 5,536,410 | A | * | 7/1996 | Kitatsuji et al. ............. 210/626 |
| 5,670,055 | A | * | 9/1997 | Yu et al. ..................... 210/698 |
| 5,741,757 | A | * | 4/1998 | Cooper et al. ............... 504/153 |
| 6,001,158 | A | * | 12/1999 | Elphingstone et al. ... 106/18.31 |
| 6,165,364 | A | * | 12/2000 | Maunuksela et al. ........ 210/631 |
| 6,784,168 | B1 | * | 8/2004 | Jones et al. .................. 514/76 |
| 6,926,832 | B2 | * | 8/2005 | Collins et al. ............... 210/615 |

(Continued)

FOREIGN PATENT DOCUMENTS

GB  1 221 550  2/1971

OTHER PUBLICATIONS

International Search Report corresponding to PCT/GB 2005/002439 issued on Sep. 7, 2005, 2 pages.

*Primary Examiner*—Peter A Hruskoci
(74) *Attorney, Agent, or Firm*—Buchanan, Ingersoll & Rooney P.C.

(57) ABSTRACT

The invention provides the use of an effective amount of a non-oxidizing water-soluble biocide in the improvement of sludge quality by reducing the sludge tendency towards bulking, wherein the biocide comprises an alkyl-substituted phosphonium compound, an alkyl-substituted phosphine, an alkyl-substituted phosphine condensate, or a polymeric quaternary ammonium compound.

28 Claims, 4 Drawing Sheets

U.S. PATENT DOCUMENTS

| | | |
|---|---|---|
| 7,214,292 B2 * | 5/2007 | Bowdery et al. ............... 162/78 |
| 7,407,590 B2 * | 8/2008 | Ludensky et al. ........... 210/698 |
| 2003/0052059 A1 * | 3/2003 | Boyette et al. .............. 210/626 |

* cited by examiner

SLUDGE QUALITY

This application is an application under 35 U.S.C. Section 371 of International Application Number PCT/GB2005/002439 filed on Jun. 21, 2005.

The present invention relates to the use of water-soluble biocides in the improvement of sludge quality and in particular to the use of non-oxidising water-soluble biocides in the improvement of sludge quality by reducing the sludge tendency towards bulking.

In the processing of wastewater from both industrial and municipal sources, the quality of the sludge can vary. It is preferred to have good quality sludge that does not have a tendency towards bulking and that has a relatively high settling speed, which can therefore easily be separated out from clear water. Otherwise, the discharged water is likely to be turbid and will therefore contaminate the water into which it is discharged (e.g. river water).

In particular, it is preferable for there to be relatively low levels of filamentous bacteria present in the sludge and/or relatively short filamentous bacteria, as the presence of filamentous bacteria, and in particular those of longer lengths, can provoke sludge bulking.

It is also preferable for there to be protozoa and/or other higher organisms, including worms, present in the sludge as these improve the quality of the sludge. This is because many protozoa and rotifers in suspended-growth systems are predators, which feed on bacteria; it is therefore believed that they enhance both flocculation and clarification because of their feeding on dispersed organisms and organics.

Accordingly there is a need for ways of improving the quality of sludge.

The present invention provides, in a first aspect, the use of an effective amount of water-soluble biocide in the improvement of sludge quality.

In particular, the invention provides the use of an effective amount of a non-oxidising water-soluble biocide in the improvement of sludge quality by reducing the sludge tendency towards bulking, wherein the biocide comprises an alkyl-substituted phosphonium compound, an alkyl-substituted phosphine, an alkyl-substituted phosphine condensate, or a polymeric quaternary ammonium compound.

Preferably, the water-soluble biocide is used in the improvement of sludge quality by reducing the sludge volume index (SVI) as measured by the Mohlman index to 200 cm$^3$/g or less, preferably to 180 cm$^3$/g or less, more preferably to 170 cm$^3$/g or less, most preferably to 150 cm$^3$/g or less, for example 140 cm$^3$/g or less.

Preferably, the water-soluble biocide is used in the improvement of sludge quality by reducing the levels of filamentous bacteria. In the case of filamentous bulking characterized by a high SVI (>300 cm$^3$/g), the reduction of filamentous bacteria can be detected through a significant decrease of SVI, to preferred levels as mentioned above. The levels of filamentous bacteria may be reduced permanently, by killing the bacteria, or temporarily, e.g. by inactivating the bacteria. It is preferred that the water-soluble biocide is added in an amount effective to reduce the levels of filamentous bacteria temporarily, rather than an amount effective to actually kill the bacteria. This permits a lower dose of biocide to be used, which is more economic. Further, the use of a biocide at a level to kill bacteria may unduly affect the activity of the sludge, which at a number of stages in the wastewater treatment process is undesirable.

The reduction of filamentous bacteria may preferably be such that the SVI is reduced to 80% or less of the pre-treatment SVI value, preferably 70% or less, more preferably 60% or less, such as 55% or less, for example 50% or less.

In particular, it is preferred that the water-soluble biocide is used in the improvement of sludge quality by reducing the levels of one or more filamentous bacteria selected from the following genii: *Thiothrix* sp., Type 021N, *H. hydrossis*, Type 0092, *N. limicola*, Type 0041, and Type 0803.

Alternatively or additionally, the water-soluble biocide may preferably be used in the improvement of sludge quality by reducing the levels of long chained filamentous bacteria. The levels of long chained filamentous bacteria may be reduced permanently, by killing long chained filamentous bacteria, or temporarily, e.g. by inactivating long chained filamentous bacteria or by breaking long chained filamentous bacteria into shorter filaments. It is preferred that the water-soluble biocide is added in an amount effective to reduce the levels of long chained filamentous bacteria temporarily, rather than an amount effective to actually kill the bacteria. This permits a lower dose of biocide to be used, which is more economic. Further, the use of a biocide at a level to kill bacteria may unduly affect the activity of the sludge, which at a number of stages in the wastewater treatment process is undesirable.

Preferably, the levels of long chained filamentous bacteria having a length of >500 μm are reduced, for example the levels of long chained filamentous bacteria having a length of >600 μm may preferably be reduced. Preferably, the levels of long chained filamentous bacteria having a length of >500 μm are reduced by a factor of 2 or more, more preferably a factor of 3 or more, most preferably a factor of 4 or more, for example a factor of about 5.

It is particularly preferred that the water-soluble biocide is used in the improvement of sludge quality by reducing the levels of filamentous bacteria such that the total length of filaments per microscopic field is reduced. Preferably, the total length of filaments per microscopic field is reduced by a factor of 2 or more, more preferably a factor of 3 or more, most preferably a factor of 5 or more, such as a factor of 7 or more, for example a factor of about 10.

Preferably, the effective amount of water-soluble biocide used in the improvement of sludge quality does not decrease the levels of protozoa and/or other higher organisms, and may even increase the levels of protozoa and/or other higher organisms.

Preferably, the effective amount of water-soluble biocide used in the improvement of sludge quality does not decrease the activity of the sludge, and may increase the activity of the sludge.

The effective amount of water-soluble biocide used is suitably from 0.01 to 5000 ppm, for example from 0.05 to 3000 ppm, such as from 0.1 to 1000 ppm. Preferably, the amount used is from 0.05 to 500 ppm, for example from 0.1 to 300 ppm, such as from 0.5 to 200 ppm. More preferably, the amount used is from 0.1 to 100 ppm, for example from 0.5 to 80 ppm, such as from 0.75 to 50 ppm, e.g. from 1 to 40 ppm. Most preferably, the amount used is from 0.1 to 30 ppm, preferably from 0.5 to 25 ppm, for example from 0.75 to 20 ppm, such as from 1 to 15 ppm. In one embodiment, the amount used is from 0.5 to 20 ppm, preferably from 1 to 10 ppm, for example from 2 to 7 ppm, such as from 3 to 5 ppm. The appropriate amount will of course depend upon the initial quality of the sludge to be treated and the desired improvement in quality.

Both oxidising and non-oxidising water-soluble biocides are known in the art. The water-soluble biocide used in the present invention is non-oxidising. A non-oxidizing biocide is believed to react less with inert organic matter and therefore act more specifically on bacteria.

The biocide should be one that is suitable for application to any aqueous system, and therefore should preferably have low environmental toxicity. For example, a biocide that has a short persistence in the environment and/or good biodegradability may be preferred.

Accordingly, biocides known to not be suitable for use in aqueous environments, such as biocides having a relatively high environmental toxicity, (for example phenolic compounds, e.g. 2,4-dinitrophenol and para-nitrophenol; cyanide containing compounds such as potassium cyanide; tin compounds such as triphenyl tin acetate; and toluene) are not used in the present invention.

The non-oxidising water-soluble biocide used in the present invention comprises an alkyl-substituted phosphonium compound, or an alkyl-substituted phosphine, or an alkyl-substituted phosphine condensate, or a polymeric quaternary ammonium compound.

The non-oxidising water-soluble biocide may, if desired, comprise mixtures of two or more such compounds. Alternatively, the non-oxidising water-soluble biocide may comprise only one such compound.

In one embodiment the non-oxidising water-soluble biocide used in the present invention comprises an alkyl-substituted phosphonium compound, or an alkyl-substituted phosphine, or an alkyl-substituted phosphine condensate.

More preferably the non-oxidising water-soluble biocide comprises an alkyl-substituted phosphonium compound of formula (I), or an alkyl-substituted phosphine of formula (II) or a condensate of formula (III):

wherein:
X is an anion;
n is the valency of X represented by m;
each A can be the same or different and is selected from OH, $OR^a$, $SO_3R^a$, $PO_3R^a_2$, COOH, $COOR^a$, $SO_3H$, $PO_3H_2$, $CH_2COOH$, substituted alkyl, aryl and substituted amino groups;

each R, and each $R^a$ (when present) in each A group, is independently selected from hydrogen, a $C_1$ to $C_{20}$ alkyl, aryl, substituted alkyl or aryl, carboxy or carboxy ester; wherein each $CR_2$ group may be the same or different;

R" is a divalent hydrocarbon radical having from 2 to 20 carbon atoms and is optionally substituted with one or more substituents selected from the group consisting of halogen, hydroxy, carboxy, amino, alkylamino, or $PR^1_mCH_2OH$ groups and/or optionally interrupted by one or more ether or carbonyl linkages;

each $R^1$ is independently a monovalent hydrocarbon radical having from 1 to 25 carbon atoms and optionally substituted with one or more substituents selected from the group consisting of halogen, hydroxy, carboxy, amino, alkylamino, or $PR^1_vCH_2OH$ groups and/or optionally interrupted by one or more ether or carbonyl linkages; and in formula (III) each v is 1 or 2, k is from 0 to 10 (e.g. from 1 to 10), x is the number of groups in the molecule having v=2 and X is a compatible anion of valency y such that the compound is water-soluble.

X is preferably selected from the group consisting of chloride, sulphate, phosphate, acetate and bromide.

In a particularly preferred embodiment, the alkyl-substituted phosphonium compound is tetrakis (hydroxymethyl) phosphonium sulphate (THPS). However, the alkyl-substituted phosphonium compound may also preferably be selected from the group consisting of tetrakis (hydroxymethyl) phosphonium chloride, tetrakis (hydroxymethyl) phosphonium bromide, tetrakis (hydroxymethyl) phosphonium acetate, and tetrakis (hydroxymethyl) phosphonium phosphate.

The alkyl-substituted phosphine is preferably tris (hydroxymethyl) phosphine (THP).

The condensate is preferably a condensate of tris (hydroxyorgano) phosphine, more preferably a condensate of tris (hydroxyorgano) phosphine with a nitrogen-containing compound.

The nitrogen-containing compound is preferably urea. Alternatively the nitrogen-containing compound may be selected from a $C_{1-20}$ alkylamine, dicyandiamide, thiourea and guanidine.

In one embodiment the non-oxidising water-soluble biocide may comprise a polymeric quaternary ammonium compound, for example polyoxyethylene (dimethylimino) ethylene dichloride. As a suitable polymeric quaternary ammonium compound, GLOKILL PQ (available from Rhodia) may be mentioned.

The biocide may if desired additionally comprise other water-soluble biocidal compounds. For example, it may further comprise a non-oxidising compound selected from:

quaternary ammonium compounds, e.g. dodecyl trimethyl ammonium chloride, cetyltrimethylammmonium bromide, benzalkonium chloride, didecyldimethylammonium chloride and alkyldimethylbenzylammonium chloride;

polymeric biguanide hydrochlorides, e.g. polyhexamethylenebiguanide hydrochloride, dodecylguanidine hydrochloride;

tris(hydroxymethyl)nitromethane;
4,4-dimethylozazolidine;
phenoxypropanol;
phenoxyethanol;
glyoxal;
acrolein;
aldehydes, e.g. formaldehyde, glutaraldehyde;
triazines, e.g. 1,3,5-tris(2-hydroxyethyl)-1,3,5-hexahydrotriazine;
quaternary phosphonium compounds, e.g. tributyltetradecylphosphonium chloride and tetradecyl tributyl phosphonium chloride;
2-bromo-4-hydroxyacetophenone;
carbamates, e.g. sodium N-dimethyldithiocarbamate, disodium ethylene bisdithiocarbamate;
tertbuthylazine;
tetrachloro-2,4,6-cyano-3-benzonitrile;

thiazole and isothiazole derivatives such as 2-methyl-4-isothiazolin-3-one, 5-chloro-2-methyl-4-isothiazolin-3-one, 5-chloro-2-methyl-3(2H)-isothiazolone and 1,2-benzisothiazolin-3-one;

compounds with activated halogen groups such as 2-bromo-2-nitro-propan-1,3-diol;

bis chloromethyl sulphone, and methylene bis thiocyanate.

The water-soluble biocide may additionally be formulated with one or more of the following chemicals conventionally used in wastewater treatment:

a surfactant;

an antifoam;

a scale inhibitor;

a corrosion inhibitor;

a biocide;

a flocculant;

a dewatering aid; and a dispersant.

The sludge may be from industrial or municipal effluent. In particular the sludge may be from industrial processes, including paper production, food processing, and chemical industry processes, or from domestic and institutional habitations and the like.

The water-soluble biocide may suitably be used during a water treatment process and may be used at any suitable point during such a process. In particular, the water-soluble biocide may suitably be used during a water treatment process carried out in a wastewater treatment plant. The water-soluble biocide is preferably used during a water treatment process after the aerobic digestion stage, for example, in a settling tank or lagoon. However, alternatively, the water-soluble biocide could be used during a water treatment process before or during the aerobic digestion stage.

The water-soluble biocide may be used by continuous or discontinuous addition to the sludge. Preferably, the water-soluble biocide is added discontinuously, for example by the use of one or more discrete additions of the biocide as required.

In one embodiment, one discrete addition of an effective amount of biocide to the sludge is effected, and then one or more further discrete additions of an effective amount of biocide to the sludge are effected as required. In particular, after the first discrete addition of biocide the quality of the sludge may be monitored (e.g. by monitoring the SVI), and each time the quality fails to meet a desired criterion (e.g. one of the preferred criteria to be achieved as discussed above, such as SVI as measured by the Mohlman index of 200 cm$^3$/g or less) a further discrete addition of an effective amount of biocide to the sludge is effected.

Accordingly, there may be two or more discrete additions of an effective amount of biocide to the sludge, and the additions may be separated by any suitable length of time. This length of time may, in one embodiment, be 12 hours or more, such as 24 hours or more, for example 48 hours or more.

In a preferred embodiment, the water-soluble biocide is added by the use of one or more discrete additions as required at a settling tank or lagoon, for example by addition at the entry to a settling tank or lagoon.

The invention also provides a method for the improvement of sludge quality by reducing the sludge tendency towards bulking, wherein the method comprises adding a non-oxidising water-soluble biocide to sludge, wherein the biocide comprises an alkyl-substituted phosphonium compound, an alkyl-substituted phosphine, an alkyl-substituted phosphine condensate, or a polymeric quaternary ammonium compound.

The preferred features of this method are as discussed above in relation to the use of the present invention.

The invention will now be described merely by way of example with reference to the following examples and accompanying figures, of which.

Figure 1:
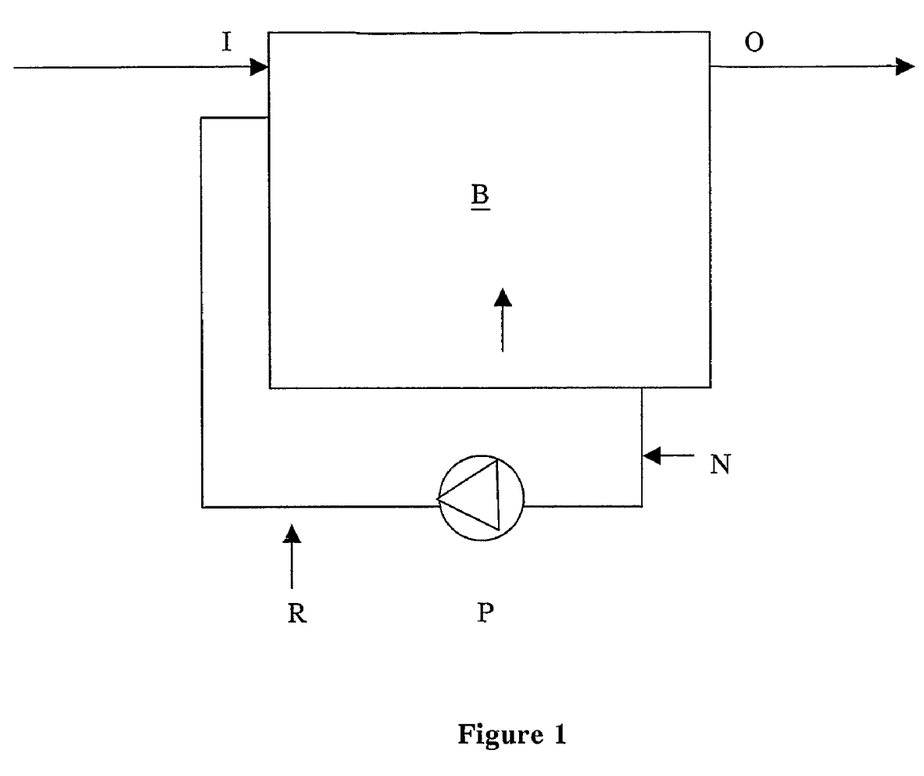
FIG. 1 is a diagram illustrating the process of flash mixing.

Referring to FIG. 1 a typical bioreactor B is shown with a recirculating line R into which the water-soluble biocide may be injected. The bioreactor contains sludge, which is essentially a mass of typical wastewater treatment microorganisms such as bacteria, protozoa, worms and fungi. The bioreactor B has an inlet I for wastewater and an outlet O for treated water. The sludge is extracted from the bioreactor into the recirculation line R by means of a pump P. Typically, a peristaltic pump is used. The candidate water-soluble biocide is introduced to the sludge in the recirculating line via a needle connected to a syringe pump N. It will be appreciated that in a commercial scale bioreactor the water-soluble biocide will be introduced via a tee-junction or an injection quill and a progressive cavity pump may replace the peristaltic pump. This enables direct contact of the sludge with the water-soluble biocide. The water-soluble biocide may be introduced into the recirculation line R at a location behind or ahead of the pump P.

However, it will be appreciated that the implementation of the invention is not restricted to using the method of "flash mixing" and other dosing methods may be used if so desired.

EXAMPLE 1

Semi-Continuous Pilot Study with Flash Mixing

1. Equipment

Figure 2:
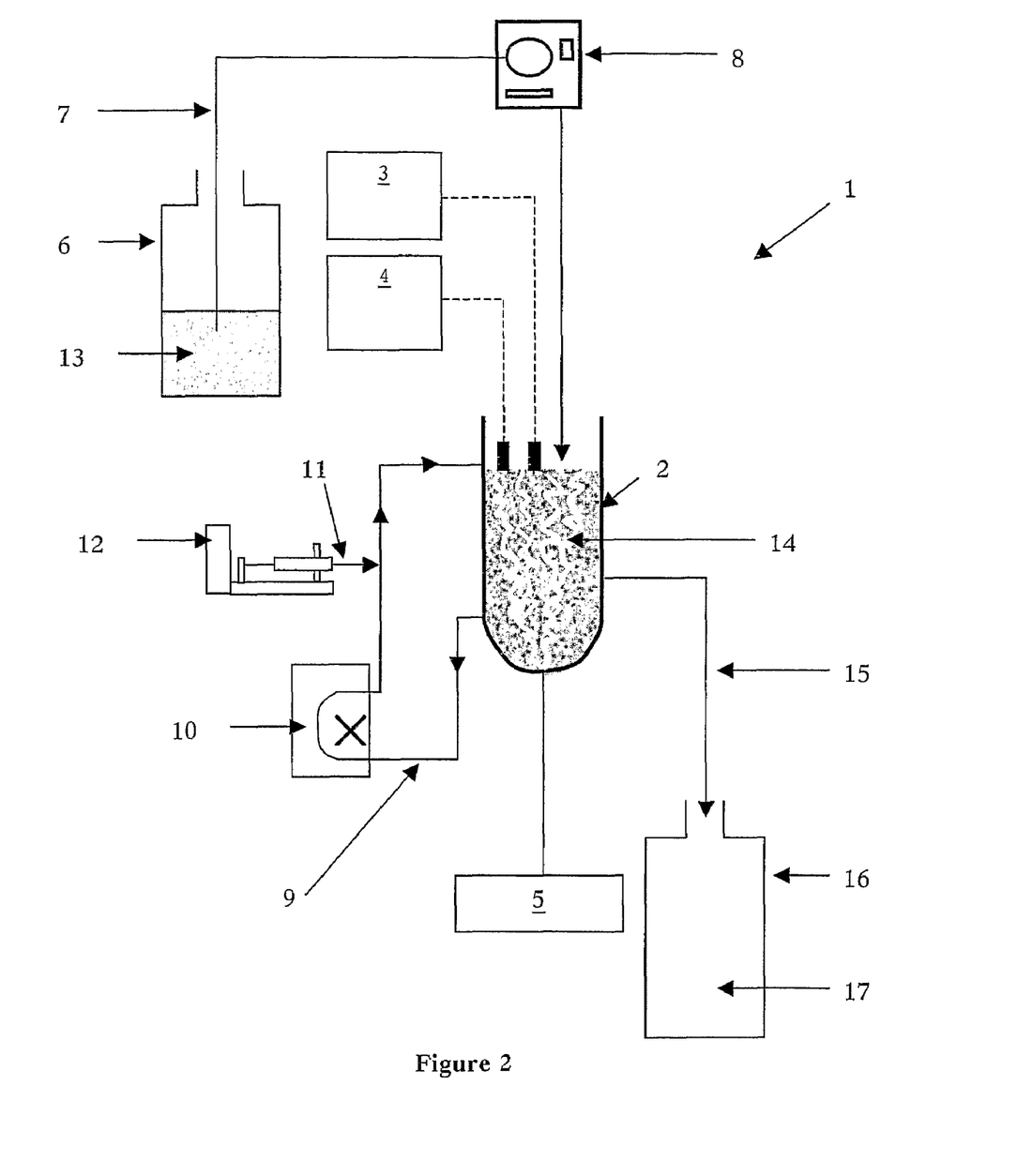
FIG. 2 is a diagram of a semi-continuous chemostat reactor system.

A series of semi-continuous chemostat reactors was constructed to simulate wastewater treatment processes. The arrangement of a semi-continuous chemostat reactor is shown in FIG. 2.

The central part of the equipment is the biological chemostat reactor 1. The reactor vessel 2 is made of glass, with an internal volume of 10 liters and is fitted with pH 3 and dissolved oxygen 4 sensors and an air sparge 5. This contains the sludge, which is, essentially, a mass of typical wastewater treatment microorganisms. The reactor operates at an ambient temperature (approximately 20° C.).

Simulated wastewater 13 is contained in a separate vessel 6 and maintained at 4° C. to prevent microbial spoilage. It is transferred into the reactor via a supply line 7 and a peristaltic pump 8.

A recirculating line 9 is provided on the reactor comprising a length of flexible silicone tubing and a peristaltic pump 10. The peristaltic pump extracts the sludge from the reactor into the recirculation line. The candidate water-soluble biocide is introduced into this line 9 through a needle 11, which is fed by a syringe pump 12. Using this system it is possible to achieve "flash mixing" which ensures rapid contact of the water-soluble biocide with the sludge microorganisms. The internal diameter of the recirculating line was 8 mm and the flow velocity was 0.5 meters per second, which gave a contact time, between candidate water-soluble biocide and sludge of 3 seconds before it re-entered the reactor.

Treated effluent 17 is removed from the reactor into a collecting vessel 16 via an outlet line 15.

2. Procedure

The reactor was charged with sludge obtained from the Municipal wastewater treatment works at Courly-Lyon, in France. This sludge provided the "seed" to start the process off. The reactor was then filled, to the 5 liter mark, with simulated wastewater, adjusted to approximately pH 7.5, and aeration was commenced. The reactor was continuously fed, at a rate of 800 ml per day, with simulated wastewater made to the recipe shown in Table B.

Each weekday (i.e. 5 times per week), 13.3% of the bioreactor contents were withdrawn to maintain the equilibrium. This ensured a sludge age in the region of 7.5 days.

Also, each weekday, after the adjustments described in the preceding paragraph, candidate water-soluble biocide (as a dilute solution) was injected into the system via the flash mixing recirculating line. The dilute solution was prepared by dissolving 10 grams of sodium hydrogen carbonate in approximately 900 ml of deionised water then adding 5 grams of candidate water-soluble biocide and mixing well. The mixture was then made up to 1 liter with deionised water. The appropriate volume of this dilute solution was injected to achieve the required dose level.

The experiment was conducted for 52 days before decommissioning the system.

3. Test Concentrations

Compound X was evaluated in the test. This compound is a 75% aqueous solution of tetrakis(hydroxymethyl)phosphonium sulphate (THPS). Two concentrations were evaluated: 2 and 4 milligrams per liter per day, as well as a control with no treatment by Compound X.

4. Results

The control (untreated) study showed a proliferation of filamentous bacteria in the sludge whereas these were substantially absent in sludge from Compound X treated systems.

There was a significantly higher concentration of protozoans and other higher organisms in the treated sludge relative to the untreated.

Compound X treatment did not impair sludge flocculation.

5. Comments

This study confirmed that Compound X flash treatment, at low dose levels, was capable of significantly improving sludge quality resulting in a sludge which would flocculate more easily, thus providing operational benefits.

TABLE B

Simulated Wastewater Composition

| Component | Concentration (mg/l) |
| --- | --- |
| Acetic Acid | 3400 |
| Sucrose | 600 |
| Yeast Extract | 1200 |
| Casein Peptone | 600 |
| Potassium Sulphate | 180 |
| Magnesium Sulphate, heptahydrate | 180 |
| Ferrous Sulphate, heptahydrate | 30 |
| Calcium Chloride, anhydrous | 20 |
| Disodium Hydrogen | 280 |
| Sodium Hydrogen Carbonate | quantity to adjust to pH 4.3 |

EXAMPLE 2

Test Tube Settling Tests

1. Procedure

Samples were taken from the semi-continuous reactors described in Example 1, 48 days after the start up of the trial, and placed into tubes.

A sample of each of the Compound X concentrations tested in the reactors of Example 1 was evaluated in this test. Accordingly, samples with 2 and 4 milligrams per liter per day treatment of Compound X were tested, as well as a control with no treatment by Compound X.

The tubes were left for a settling period of one hour to allow the sludge to settle out of the water.

2. Results

Figure 3A:
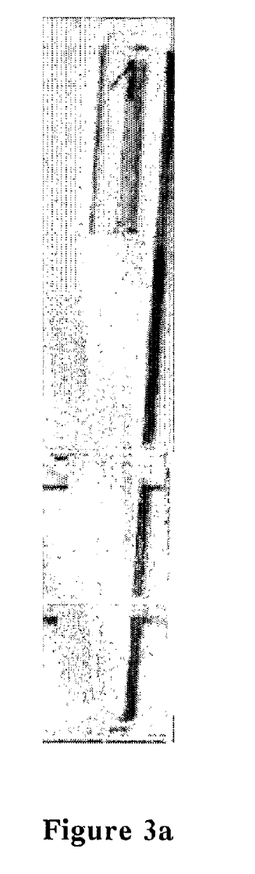
FIGS. 3A to C are photographs showing the settling of sludge achieved by adding various amounts of biocide.
Figure 3B:
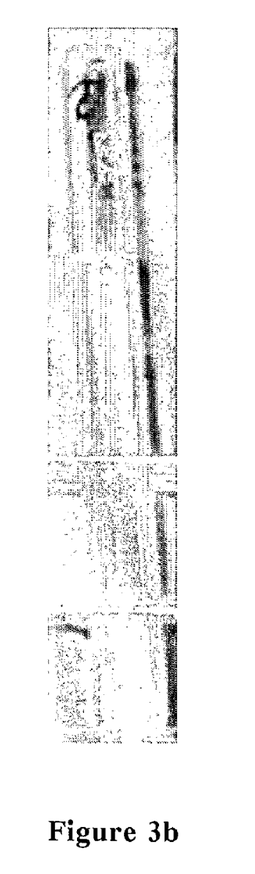
Figure 3C:
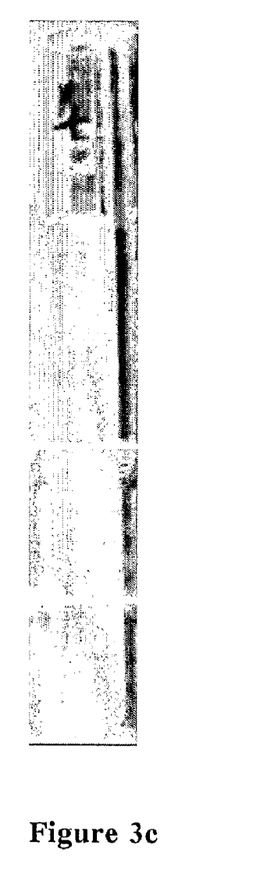

The tubes after being left for the settling period are shown in FIGS. 3A-C.

| Figure | Treatment | Observations |
| --- | --- | --- |
| 3A | None (control) | Turbid water as sludge has not settled |
| 3B | 2 mg/l/day | Clear water with settled sludge at bottom |
| 3C | 4 mg/l/day | Clear water with settled sludge at bottom |

3. Comments

This study confirmed that Compound X treatment of wastewater, at low dose levels, was capable of significantly improving sludge settling speed, thus providing operational benefits.

EXAMPLE 3

Sludge Quality Observations

1. Procedure

Samples were taken from the semi-continuous reactors described in Example 1, 48 days after the start up of the trial.

A sample of each of the Compound X concentrations tested in the reactors of Example 1 was evaluated in this test. Accordingly, samples with 2 and 4 milligrams per liter per day treatment of Compound X were tested, as well as a control with no treatment by Compound X.

The samples were observed through phase contrast microscope magnification×220.

2. Results

Figure 4A:
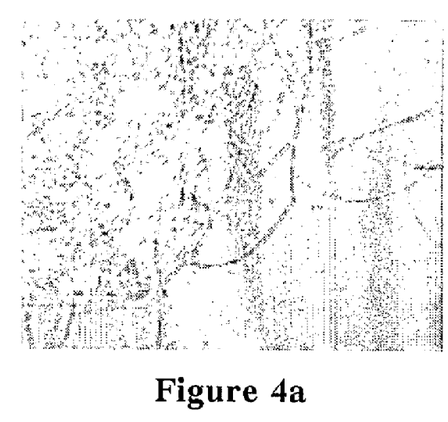
FIGS. 4A to C are photomicrographs showing sludge following addition of various amounts of biocide.
Figure 4B:
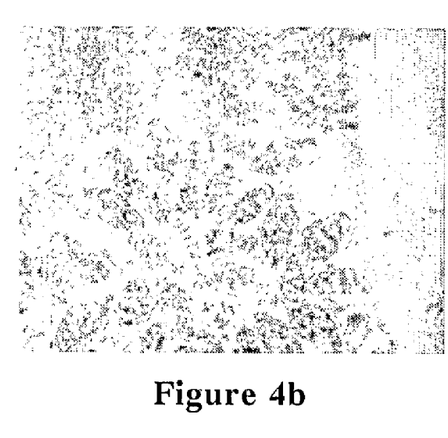
Figure 4C:
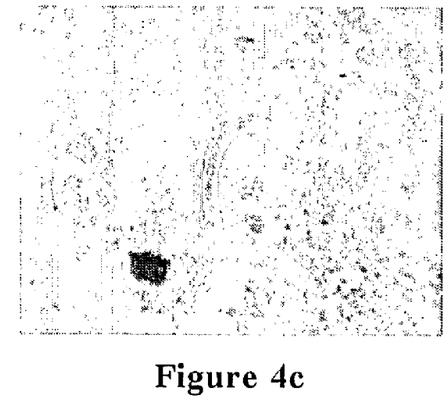

Photomicrographs of the sludge samples are shown in FIGS. 4A-C.

| Figure | Treatment | Observations |
| --- | --- | --- |
| 4A | None (control) | Long chain filamentous bacteria clearly present (threadlike mass) |
| 4B | 2 mg/l/day | No filamentous bacteria present, and protozoa clearly present |
| 4C | 4 mg/l/day | No filamentous bacteria present, and protozoa and a worm clearly present |

Reduction of filamentous bacteria and thus improved sludge settling was able to be achieved with two doses of 4 mg/l/day (i.e. a 4 mg/l dose on two consecutive days) and level of filaments remained low for more than one week without further treatment.

3. Comments

This study confirmed that Compound X treatment of wastewater, at low dose levels, was capable of significantly reducing the levels of filamentous bacterial in sludge, as well as increasing the levels of beneficial organisms such as protozoa and worms, thus providing operational benefits.

The invention claimed is:

1. A process for improving quality of sludge from industrial or municipal wastewater, by reducing bulking, comprising the step of:
adding to the sludge an effective amount of a non-oxidising water-soluble biocide said biocide comprising an alkyl-substituted phosphonium compound, an alkyl-substituted phosphine, or an alkyl-substituted phosphine condensate.

2. The process according to claim 1, wherein the sludge volume index (SVI), as measured by the Mohlman index, is being reduced to 200 cm3/g or less.

3. The process according to claim 2, wherein the SVI is reduced to 180 cm3/g.

4. The process according to any claim 2, wherein the SVI is reduced to 80% or less of the pre-treatment SVI value.

5. The process according to claim 2, wherein the SVI is reduced to 150 cm3/g or less.

6. The process according to any claim 2, wherein the SVI is reduced to 60% or less of the pre-treatment SVI value.

7. The process according to claim 1, wherein the sludge quality is being improved by reducing the level of filamentous bacteria.

8. The process according to claim 7, wherein the filamentous bacteria are *Thiothrix* sp., Type 021N, *H. hydrossis*, Type 0092, *N. limicola*, Type 0041, or *N. limicola* Type 0803.

9. The process according to claim 7, wherein the sludge quality is being improved by reducing the level of filamentous bacteria such that the total length of filaments per microscopic field is reduced.

10. The process according to claim 9 wherein the total length of filaments per microscopic field is reduced by a factor of 2 or more.

11. The process according to claim 9, wherein the total length of filaments per microscopic field is reduced by a factor of 5 or more.

12. The process according to claim 1, wherein the sludge quality is being improved by reducing by a factor of 2 or more, the level of long chained filamentous bacteria having a length of >500 μm.

13. The process according to claim 12, wherein the sludge quality is being improved by reducing by a factor of 4 or more.

14. The process according to claim 1, wherein the effective amount of water-soluble biocide used is from 0.01 to 5000 ppm.

15. The process according to claim 14, wherein the effective amount of water-soluble biocide used is from 0.1 to 100 ppm.

16. The process according to claim 14, wherein the effective amount of water-soluble biocide used is from 0.1 to 30 ppm.

17. The process according to claim 1, wherein the non-oxidising water-soluble biocide comprises an alkyl-substituted phosphonium compound of formula (I), an alkyl-substituted phosphine of formula (II) or a condensate of formula (III):

wherein: X is an anion;

n is the valency of X represented by m;

each A are the same or different and are OH, OR, $SO_3R$, $PO_3R_2$, COOH, COOR, $SO_3H$, $PO_3H_2$, $CH_2COOH$, substituted alkyl, aryl or substituted amino groups;

each R and each R (when present) in each A group, is independently hydrogen, a $C_1$ to $C_{20}$ alkyl, aryl, substituted alkyl or aryl, carboxy or carboxy ester; wherein each $CR_2$ group are the same or different;

R" is a divalent hydrocarbon radical having from 2 to 20 carbon atoms and is optionally substituted with one or more substituents which are halogen, hydroxy, carboxy, amino, alkylamino, or $PR^1mCH2OH$ groups and/or optionally interrupted by one or more ether or carbonyl linkages;

each $R^1$ is independently a monovalent hydrocarbon radical having from 1 to 25 carbon atoms and optionally substituted with one or more substituents being halogen, hydroxy, carboxy, amino, alkylamino, or $PR^1VCHOH$ groups and/or optionally interrupted by one or more ether or carbonyl linkages; and in formula (III) each v is 1 or 2, k is from 0 to 10, x is the number of groups in the molecule having v=2 and X is a compatible anion of valency y such that the compound is water-soluble.

18. The process according to claim 17, wherein the alkyl-substituted phosphonium compound is tetrakis (hydroxymethyl) phosphonium sulphate (THPS).

19. The process according to claim 17, wherein the alkyl-substituted phosphonium compound is tetrakis (hydroxymethyl) phosphonium chloride, tetrakis (hydroxymethyl) phosphonium bromide, tetrakis (hydroxymethyl) phosphonium acetate, or tetrakis (hydroxymethyl) phosphonium phosphate.

20. The process according to claim 17, wherein the alkyl-substituted phosphine is tris (hydroxymethyl) phosphine (THP).

21. The process according to claim 17, wherein the condensate is a condensate of tris (hydroxyorgano) phosphine with a nitrogen-containing compound.

22. The process according to claim 21, wherein the nitrogen-containing compound is urea.

23. The process according to claim 1, wherein the water-soluble biocide is further formulated with a surfactant; an antifoam; a scale inhibitor; a corrosion inhibitor; a biocide; a flocculent; a dewatering aid; or a dispersant.

24. The process according to claim 1, wherein the water-soluble biocide is used during a water treatment process carried out in a wastewater treatment plant.

25. The process according to claim 24, wherein the water-soluble biocide is used during a water treatment process after an aerobic digestion stage.

26. The process according to claim 25, wherein the soluble biocide is used during a water treatment process in a settling tank or lagoon.

27. The process according to claim 1, wherein the water-soluble biocide is added discontinuously.

28. The process according to claim 1, wherein the effective amount of water-soluble biocide used is from 0.05 to 500 ppm.

* * * * *